United States Patent [19]

Walsh et al.

[11] Patent Number: 4,612,247
[45] Date of Patent: Sep. 16, 1986

[54] MAGNETIC CELLULOSE-DERIVATIVE STRUCTURES

[75] Inventors: Myles A. Walsh, Falmouth; Robert S. Morris, Fairhaven, both of Mass.

[73] Assignee: Cape Cod Research, Inc., Buzzards Bay, Mass.

[21] Appl. No.: 624,956

[22] Filed: Jun. 27, 1984

[51] Int. Cl.$^4$ .................................. B32B 5/16; C12N 1/02
[52] U.S. Cl. ............................. 428/402; 210/688; 210/691; 427/128; 428/321.5; 428/407; 428/900; 435/261
[58] Field of Search ............ 428/407, 900, 321.5, 428/402, 402.24; 427/128; 435/261

[56] References Cited

U.S. PATENT DOCUMENTS

| | | | |
|---|---|---|---|
| 3,464,920 | 9/1969 | Pirson et al. | 210/29 |
| 3,560,378 | 2/1971 | Weiss et al. | 210/36 |
| 3,657,119 | 4/1972 | Turbeville | 210/36 |
| 3,696,032 | 10/1972 | Haensel | 210/42 |
| 3,846,404 | 11/1974 | Nichols | 260/230 |
| 3,970,518 | 7/1976 | Giaever | 424/12 |
| 3,985,298 | 10/1976 | Nichols | 428/403 |
| 4,029,726 | 6/1977 | Nichols | 264/41 |
| 4,075,391 | 2/1978 | Berg et al. | 428/900 |
| 4,105,572 | 8/1978 | Gorondy | 427/47 |
| 4,201,831 | 5/1980 | Slusarczuk et al. | 428/403 |
| 4,254,201 | 3/1981 | Sawai et al. | 430/311 |
| 4,276,179 | 6/1981 | Soehngen | 210/679 |
| 4,279,756 | 7/1981 | Weiss et al. | 210/667 |
| 4,284,511 | 8/1981 | Weitzen | 210/661 |
| 4,285,819 | 8/1981 | Yen et al. | 210/679 |
| 4,294,705 | 10/1981 | Hellestam | 210/695 |
| 4,295,971 | 10/1981 | Khahafalla et al. | 210/695 |
| 4,298,478 | 11/1981 | Watson et al. | 210/695 |
| 4,303,531 | 12/1981 | Kawabata et al. | 210/663 |
| 4,307,169 | 12/1981 | Matkan | 430/107 |
| 4,356,093 | 10/1982 | Abercrombie et al. | 210/695 |
| 4,450,221 | 5/1984 | Terada et al. | 430/124 |

FOREIGN PATENT DOCUMENTS 0193687 11/1983 Japan .................................. 435/261

*Primary Examiner*—Herbert J. Lilling
*Attorney, Agent, or Firm*—Pahl, Lorusso & Loud

[57] ABSTRACT

Structures to serve as selective magnetic sorbents are formed by dissolving a cellulose derivative such as cellulose triacetate in a solvent containing magnetic particles. The resulting solution is sprayed as a fine mist into a chamber containing a liquid coagulant such as n-hexane in which the cellulose derivative is insoluble but in which the coagulant is soluble or miscible. On contact with the coagulant, the mist forms free-flowing porous magnetic microspheric structures. These structures act as containers for the ion-selective or organic-selective sorption agent of choice. Some sorbtion agents can be incorporated during the manufacture of the structure.

17 Claims, 3 Drawing Figures

MAGNETIC CELLULOSE-DERIVATIVE STRUCTURES

This invention was made with Government support under Contract No. DE-ACO2-83ER80030 awarded by the Department of Energy. The Government has certain rights in this invention.

BACKGROUND OF THE INVENTION

The present invention relates to a structure and method of preparing structures to serve as selective magnetic sorbents or bioplatforms and a method of using the sorbents in the removal of soluble materials such as, for example, lead, copper, or mercury cations or tungstate, uranyl, or cyanide anions from aqueous solutions. Specifically, the present invention relates to easily recoverable, microspheric magnetic structures comprising magnetic materials encapsulated in microporous shells produced through the gelling of a cellulose derivative. The structures can be filled with agents of choice.

Considerable interest exists in commercial and government facilities to develop a low cost, fully effective, recyclable means for total removal of toxic materials from waste water streams of all types, including agricultural run-off and geothermal brines. Similar interest exists in recovering strategic materials from natural brines and from industrial process streams.

The rate at which ion-exchange beads absorb or adsorb ions from dilute solution is directly proportional to the surface area of the beads and thus for a given weight of beads is inversely proportional to the size of the beads. Therefore, for a given weight of beads, increases in reaction rates can be achieved even at low concentration by raising the number and reducing the size of the beads. Conventional resins of small bead size are, however, very difficult to recover from process streams, especially when they become commingled with particulate waste matter. Since incorporation of one or more magnetic particles within small ion-exchange beads greatly increases the ease at which they can be recovered from process solutions, there have been many attempts to produce small, magnetic ion-exchange beads.

Chemically reactive magnetic microspheres have heretofore been constructed either through chemical surface treatment of solid magnetic dust or by the in-situ formation of small magnetic particles within gelled ion-exchange material. For example, magnetic particles have been encapsulated in a synthetic polymer onto which desirable functional groups for ion-exchange were grafted.

Mucopolysaccharides such as chitosan have been dissolved in acidified mixtures of iron chlorides. The addition of base causes the simultaneous formation of solid magnetite particles and the precipitation of the chitosan encapsulating the magnetic particles.

However, either economic or technical difficulties have prevented the widespread commercial application of magnetic ion-exchange structures. In practice, selectivity is very important to the economics of any ion-exchange process. This is especially true when the targeted species is dissolved in water rich in other ions. In general, the prior art has not been able to produce a structure with a magnetic core which has low cost, small size, and which can be tailored to be ion-specific to a variety of ions.

SUMMARY OF THE INVENTION

The present invention involves a very effective, low cost magnetic cellulose-derivative structure. The magnetic structures in accordance with this invention are in the form of small magnetic particles dispersed in microporous beads (or spheres) of a gelled cellulose derivative. These structures are filled with a desired ion-specific exchange liquid or solid or a desired microorganism or biologically derived agent prior to use. Since the porous structure serves merely as a container which is magnetic, the function of the structure is determined entirely by the choice of the reactive material with which it is filled.

It is an object of the present invention, therefore, to recover targeted ions from water, whether fresh, brackish, salt or at least partially waste water, by dispersing the microbeads of the present invention into the water, by collecting the microbeads magnetically after the specific ions to be bound are picked up in a predetermined concentration by the microbeads, by mixing the microbeads now loaded with the targeted ions with a suitable washing fluid, by collecting the microbeads magnetically from the washing fluid now loaded with ions, and by reusing the microbeads by reinserting them back into additional water containing ions to be recovered. The washing fluid is selected according to the kinds of ions extracted and according to the kind of ion-specific absorbent stored in the porous cellulose derivative matrix. This washing fluid, according to the particular application, can be concentrated in a second stage by a suitable ion-exchange agent.

In one type of process, the microbeads of the present invention can be used for a single sorption process (for instance, for highly radioactive wastes), where it is undesirable to wash out the retained material back into an elution solution. In such a case, the ion-specific absorbent can be burnt in a suitable apparatus at temperatures of about 500° to 800° C., and the volume of the contaminated solid phase can thus be substantially reduced prior to storage in suitable storage places for radioactive wastes.

A further object of this invention is to provide a microbead suitable for absorbing organics from water. To remove dissolved organics from waste water, the microporous structure of this invention can be readily filled with a water-insoluble organic liquid. This liquid can be chosen from those liquids having large distribution coefficients for the targeted organic species dissolved in water. To absorb hydrophobic organic material, structures filled with such compounds as carnuba wax can be dispensed onto the organic material and then collected for disposal or salvaging of the organic material.

Yet another object of this invention is the use of the microporous magnetic structure as a retrievable platform for bioconversion of organic compounds in bioreactors. In one such use, yeast of the strain *Saccharomyces cerevisiae* can be incorporated into the structure and suspended in a continuous flow bioreactor while the yeast converts glucose to ethanol. A bioreactor similar to that in Sada et al., *Biotech. & Bioeng.* 23:25-61-2567 (1981), may be used.

These and many other features and attendant advantages of the invention will become readily apparent as the invention becomes better understood by reference to the following drawings and detailed description.

DESCRIPTION OF THE PREFERRED EMBODIMENT

At the outset, the invention is described in its broadest overall aspects with a more detailed description following. In its simplest terms, the structure of the present invention is a porous shell or sphere housing a magnetic particle and a reactive agent.

Figure 1:
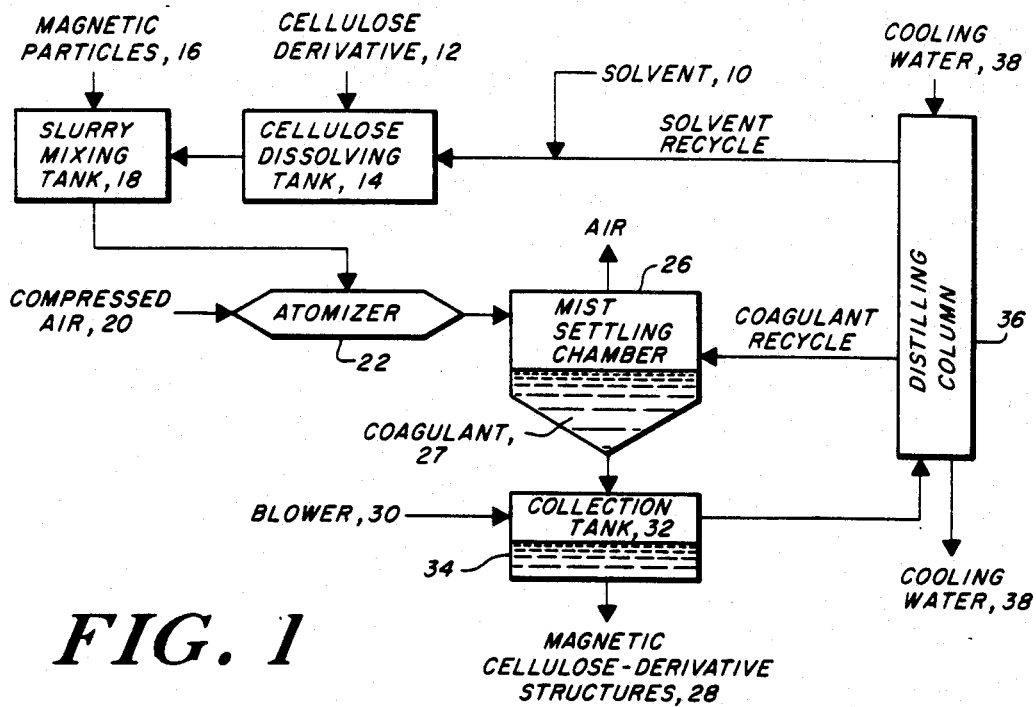
FIG. 1 is a diagrammatic flow sheet illustrating a process for making beads in accordance with the present invention wherein a solution of a dissolved cellulose-derivative containing suspended solid magnetic or magnetized particles is sprayed as a fine mist into a chamber containing a liquid coagulant.
Figure 2:
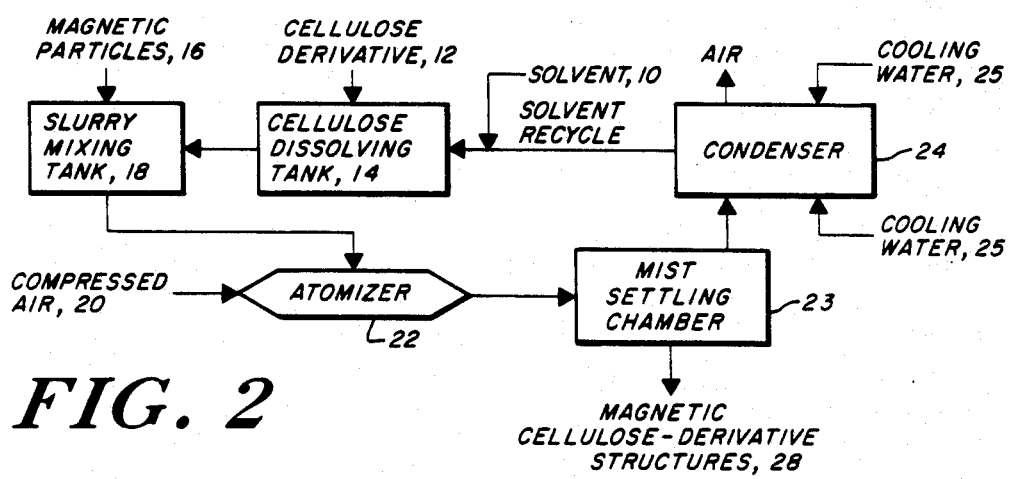
FIG. 2 is a diagrammatic flow sheet illustrating a process for making beads in accordance with the present invention wherein solid magnetic or magnetizable particles are stirred into a solution containing a dissolved cellulose derivative and the solvent is allowed to evaporate; and, FIG. 3 is a cross-sectional diagrammatical view of a magnetic cellulose-derivative structure capable of containing a chemical agent in accordance with the present invention.

As depicted in FIGS. 1 and 2, the magnetic structures in accordance with the present invention are manufactured by first providing a solvent 10 and then dissolving a cellulose derivative 12 in the solvent in a cellulose dissolving tank 14. Magnetic particles 16 are then stirred into this solution in a slurry mixing tank 18 to produce a suspension of such particles in the solution. The resulting suspension may be sprayed with an air-powered atomizer 20, 22 as a fine mist into a chamber. FIG. 2 depicts a process wherein the mist settles in a chamber 23 and the solvent is allowed to evaporate to produce the magnetic cellulose-derivative structure 28. The solvent can be recycled using a condenser 24 and cooling water 25.

Alternatively, as illustrated in FIG. 1, the mist can be caught in a container 26 filled with a liquid coagulant 27 which does not dissolve the cellulose derivative, but in which the solvent is highly soluble. By way of example, n-hexane is a preferred coagulant for dissolving methylene chloride (solvent for cellulose derivative). On contact with the coagulant 27, the mist rapidly coagulates into microscopic, free-flowing microbeads of a microporous cellulose derivative, termed magnetic cellulose-derivative structures 28.

FIG. 1 further shows a method of collecting the magnetic cellulose-derivative structures wherein heat from a blower 30 is used to drive off both the coagulant and the solvent after the mixture 32 passes into a collection tank 34. This method allows the coagulant and the solvent to be recycled, such as through the use of a distilling column 36 and cooling water 38.

Figure 3:
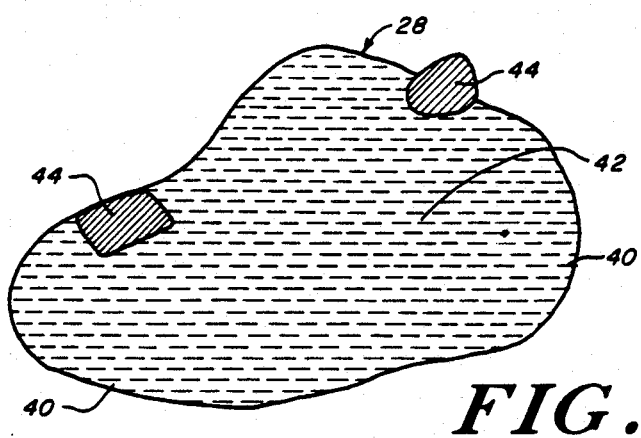

A schematic cross-sectional view of the magnetic cellulose-derivative structures 28 is provided in FIG. 3, showing the microporous cellulose 40 containing micropores 42. Most of these porous microbeads encapsulate one or more magnetic particles 44. The term "magnetic" is intended to include materials capable of being magnetized. If magnetizable particles are used they may then be magnetized in a strong magnetic field. The magnetic microbeads may be removed mechanically, as by centrifuging or settling, but are readily and efficiently removed magnetically from the porous microbeads which do not contain magnetic particles.

In accordance with the present invention, the microbeads serve as containers for ion-selective or organic-selective liquids and solids which have magnetic properties. Some selective agents can be incorporated into the structures during the manufacture of the structures, as is described in Example 4. In this example, an organic-selective agent such as carnuba wax is mixed into the suspension of magnetic particles, dissolved cellulose derivative and solvent before spraying to form structures which are magnetic and which contain the reactive agent. At this point it should be noted that the structure of the present invention is a container for any reactive agent which can be incorporated into it. Thus, the invention is not limited to a particular chemical or exchange agent. As is apparent to those skilled in the art, the examples which follow merely illustrate the wide range of reactive agents that can be incorporated into the structures of the present invention.

Cellulose is a naturally-occurring polysaccharide of glucose that is usually obtained from cotton or wood pulp. T. W. Graham Solomons, Organic Chemistry, 906 (2nd ed., 1980). It has the following structural formula:

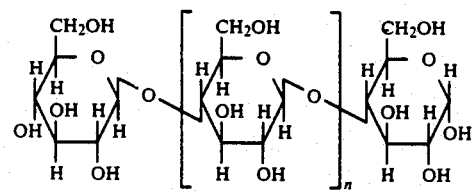

whereby n is greater than 3,000 units. Each non-terminal unit or monomer of pure cellulose has three free hydroxyl groups; the terminal units have four such groups. Derivatives of cellulose are formed by substituting some of the free hydroxyl groups with electronegative groups. Id.; see also Emil Ott, "Cellulose and Cellulose Derivatives", Volume V of *High Polymers* (Interscience Publishers, NY, NY, 1943) for an especially complete coverage of the subject.

The cellulose derivative of the present invention may be an inorganic or organic ester of cellulose; however, the preferred cellulose derivatives are those which x-ray diffraction studies show have a crystalline structure in the polymer phase. This crystalline structure results when the free hydroxyls on the cellulose chain have been largely replaced by small electronegative groups. Preferably at least two of the three free hydroxyls per unit are replaced by small electronegative groups so that the microporous cellulose-derivative structure is water-insoluble and has a porosity between 60-90 percent. A lower porosity is possible so long as the reactive agent is able to penetrate the cellulose structure. At this point it should be noted that the choice of a suitable cellulose derivative is well within the skill of those in this art. Any cellulose derivative is usable in accordance with the present invention which can be dissolved in a removable solvent so that the resulting polymer has a strong, microporous, crystalline structure that encapsulates a magnetic particle carried by the solvent. However, the preferred cellulose derivatives of the present invention are cellulose derivatives of the following formula:

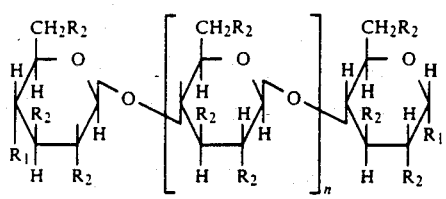

wherein n is greater than 3,000 units;

$R_1$ is usually —OH;

$R_2$ is selected from the group consisting of —$NO_2$; —$OCOCH_3$; —$OCOCH_2CH_3$; —$OCH_2CH_3$; and —OH; and the preferred average number of substitutions per unit of cellulose is at least:

| Substituted Group | Number of Substitutions | Name |
|---|---|---|
| —$NO_2$ | 2.27 | cellulose nitrate |
| —$OCOCH_3$ | 2.90 | cellulose triacetate |
| —$NO_2$, —$OCOCH_3$ | 2.25 | cellulose acetate-cellulose nitrate mixture |
| —$OC_2H_5$ | 1.5 | ethyl cellulose |
| —$OCOCH_2CH_3$ | 2.9 | cellulose tripropionate |

Microbeads can be formed at room temperature (20° C.) by dissolving cellulose derivatives in solvents such as toluene and solvents possessing properties similar to toluene including diethyl ether or low-molecular-weight chlorinated alkanes (containing six carbon atoms or less) such as methylene chloride. As will be apparent to those skilled in the art, the solvent that is selected is one that is compatible with the cellulose derivative. In other words, the solvent must dissolve the cellulose derivative selected and when removed by evaporation or dissolving in another solvent (coagulant) must result in a porous cellulose structure housing the magnetic or magnetizable particles. Any solvents which so function in conjunction with the cellulose derivative is intended to be within the scope of the present invention.

Coagulants or solvents for the solvent used to dissolve the cellulose derivative which are suitable for precipitating the cellulose derivative include water, lower alcohols (containing six carbon atoms or less) such as isopropanol, glycerin, petroleum ether, and low boiling (less than 100° C.) alkanes such as n-hexane, n-heptane, n-pentane and cyclohexane. As will be apparent to those skilled in the art, the coagulant that is selected is one that is compatible with the cellulose derivative and its solvent. In other words the coagulant must be an agent in which the solvent for the cellulose derivative is soluble and in which the cellulose derivative is insoluble.

The average size of the magnetic microbeads produced by the process of the present invention depends on the size of the drops produced by the spraying apparatus (20, 22). Large diameter particles (over 1000 microns) can be formed by spraying large drops. A fine mist produces porous magnetic microbeads with diameters between 5 and 1000 microns. Any of the numerous commercial methods can be employed for producing the spray. By way of example, but not by way of limitation, conventional paint sprayers driven by compressed air are suitable for producing both coarse and fine mists. Ultrasonic atomizing nozzles are more suitable for producing droplets with a median drop diameter of less than 30 microns.

Any magnetic or magnetizable particles of appropriate size can be used. Preferably the particles are selected from the group consisting of magnetite, barium ferrite, cobalt ferrite, nickel and magnetic stainless steel. Inexpensive magnetite is most preferred because it is commercially available as an inexpensive brick colorant. Excellent results are obtained with air floated magnetite from Foote Mineral Company, Frazer, Pa. This material contains particles whose diameters range from 40 to less than 5 microns.

The magnetic properties of the magnetic particles contained by the microbeads or spheres of the present invention can be varied over wide limits. If a very strong magnetic field is provided by a superconducting magnetic or high-gradient field source, the microbeads can contain as little as 0.1% by wt. magnetic material. Otherwise, since the microbeads need contain only a small amount of porous cellulose derivative to be effective, the microbeads can contain 90% by weight or more of magnetic material. As used throughout this specification and claims all percentages are by weight unless specified otherwise. Preferably the magnetic or magnetizable particles have a diameter of less than 50 microns.

Numerous ion-specific liquids are available which selectively extract specific cationic and anionic species from solutions containing relatively large concentrations of other ions. By way of example, but not by way of limitation, organic kerosene solutions of 7-octyl-8-hydroxyquinoline and methyl tricapryl ammonium chloride selectively extract tungstate from Searles Lake brines. Nonane 1,1,2-triphosphonic acid dissolved in dibutylphosphonate and kerosene selectively extracts uranium from concentrated phosphoric acid. Dodecylsalicylaldoxime dissolved in kerosene selectively extracts cupric ions from ground waters leached through mining dumps. Any of these ion-specific liquids can, in accordance with this invention, be filled into the micropores of the magnetic cellulose derivative microbeads by soaking the unfilled beads in the ion-specific liquid. Applying and releasing vacuum pressure may be used to augment the filling process.

Alternatively, the cellulose derivative structure can be used as a high surface area support for selective solid materials. By way of example, but not by way of limitation, the porous magnetic microbeads can be filled with $TiCl_4$ dissolved in alcohol. The filled beads can then be stirred in distilled water to produce a uniform suspension, after which solid particles of high surface area hydrous titanium oxide can be precipitated within the beads by the addition of concentrated ammonium hydroxide solution into the micropores of the cellulose derivative structure. Hydrous titanium oxide supported in the micropores of the beads can be utilized with particular advantage for the selective recovery of dissolved metals in brines and washes such as seawater, fresh water and also industrial waste water. Uranium and vanadium ions are extracted by titanium oxide. For example, hydrous titanium oxide selectively absorbs the tricarbonato uranylate anion, $UO_2(CO_3)_3^{-4}$, from sea water even though its molar concentration is eight orders of magnitude lower than the total concentration of major ions.

A further method of filling the microbeads with ion-specific material is to place the structures in a nutrient broth containing spores of fungi or microbial cultures.

For example, strains of *Penicillium chrysogenum, Mycelium sterilium, Aspergillus ochraceus* and the like cause mycelia to rapidly grow within the micropores of the beads of the present invention. These mycelium serve as a selective biosorbent for highly radioactive waste. Alternatively, many bacteria selectively remove specific ions from aqueous solution and readily grow within the micropores of the cellulose structure. For example, microbial cultures of the sea bacteria *Bacterium album* selectively remove $^{132}$Cs and $^{86}$Rb ions from sea water.

Other biologically derived sorbents may be used to fill the microbeads. For example, membrane extracts or molecular receptors such as antibodies could be bound within the microspheres, since the porosity of the structures allows a greater active agent to surface area ratio and free access of material to be removed or bound to the bound active agent.

Once the microporous magnetic structures are created and filled according to the intended use, the structures may be used in several distinct processes.

The invention is further illustrated by the following non-limiting examples.

EXAMPLE 1

A well mixed suspension of methylene chloride containing 0.04 g/cc of dissolved cellulose triacetate (Aldrich Chemical Company, Inc., greater than 92% acetylated) and 0.022 g/cc of magnetite was sprayed, using a Sears Model 364-15502 air-propelled paint sprayer, in a fine mist using mid-point setting into the atmosphere of a tank containing pure n-hexane. The magnetite consisted of particles with a diameter of ten microns or less. The resulting microbeads had an average diameter of fifty microns and each microbead contained at least one mote of magnetite.

These beads contained the same ratio by weight of cellulose triacetate to magnetite as found in the original solution prior to spraying. However, because of the coagulation of the cellulose triacetate, these microbeads contained by volume 3% magnetite, 24% cellulose triacetate and 73% void volume in the form of ultramicroscopic pores.

EXAMPLE 2

The structures described in Example 1 were filled with a 2:1 mixture by volume of refined kerosene and dodecylsalicylaldoxime. This is the most cupric ion-specific substituted oxime known and is used commercially to selectively extract copper from mine dump leach liquors. Filling was achieved by soaking the beads in this ion-exchange liquid for several days.

Tests were performed to demonstrate the efficiency of this cupric ion-specific absorbent in removing cupric ions from aqueous solutions. The concentration of cupric ions in solution was continuously monitored with a cupric ion specific electrode. The experiments consisted of vigorously stirring 100 ml of solution, adding 50 mg of beads and measuring the change in cupric ion concentration. Similar tests were made with a commercially available acidic cationic styrene-DVB ion-exchange resin (Amberlite IR-120 from Chemical Dynamics Corporation). These results are shown in Table I.

TABLE I

| Time, seconds | 0 | 20 | 40 | 60 | 80 |
|---|---|---|---|---|---|
| | Concentration in ppm of Cupric Ion in solution | | | | |
| Amberlite | 10 | 10 | 10 | 9 | 9 |
| Microbeads | 10 | 7 | 4 | 3 | 2 |

The rapid absorption by these novel absorbents is due entirely to their microscopic size. They are ten times smaller than the Amberlite beads. The cupric ion-exchange capacity of the magnetic microbeads was measured as 0.7 Meq/g.

EXAMPLE 3

Cupric ion-selective absorbents prepared according to Example 2 change color from a dull gray to a dull green on absorbing cupric ions. These beads can be returned to their original state by elution with dilute sulfuric acid. Repeated loading-elution cycles using 20 ppm cupric ion solutions at pH 4 and 2N sulfuric acid showed no measurable decay in the capacity of the beads to absorb or desorb cupric ions.

The beads in the unmagnetized state readily disperse throughout the aqueous solution. The small size and small density difference help maintain the slurry over periods of hours. However, magnetizing the beads with a magnetic field produces an immediate change in the characteristics of the suspension. The beads tend to form agglomerates consisting of numerous beads held together by magnetic forces. These agglomerates readily settle out of solution and can be readily separated from the aqueous solution by means of a cyclone separator.

EXAMPLE 4

A well-mixed solution of 50:50 (by volume) methylene chloride and chloroform containing 0.04 g/cc of cellulose triacetate and 0.022 g/cc of magnetite was combined in a 1 to 1 volume ratio with a second solution of chloroform containing 0.04 g/cc carnuba wax. The resulting yellow homogeneous solution was sprayed in a fine mist with a paint sprayer under the conditions of example 1 into an enclosed container filled with air. Evaporation of the solvent during the settling of the mist produced numerous, uniform, free flowing beads 40–60 microns in diameter, filled with carnuba wax, each containing motes of magnetite. These beads contained the same ratio by weight of cellulose triacetate, magnetite and carnuba wax as found in the starting solution.

The wax-filled magnetic microbeads dispersed and sank in a container of water upon dissolution in the water of 0.04 mg/cc of a surfactant sodium lauryl sulfate.

These structures can be used for removing hydrophobic organic material from water in a manner similar to that detailed by Ewald Pirson in U.S. Pat. No. 3,464,920, with the added advantages of the present invention being that the structures may be removed magnetically.

These examples are exemplary only and are not intended to limit the present invention. Variations and modification of the present invention will be obvious to those skilled in the art and it is intended to cover in the appended claims all such modifications and equivalents as follows in the true spirit and scope of this invention.

What is claimed is:

1. A porous magnetic structure containing at least one reactive agent comprising:
   (a) a shell formed of a microporous water-insoluble cellulose derivative, having a microporous matrix, the shell ranging in diameter from 5 to 1000 microns;
(b) one or more magnetic particles having diameters of less than 50 microns and which are encapsulated in the shell in an amount of at least 0.1 percent by weight of the shell; and
(c) at least one reactive agent supported within the microporous matrix of the cellulose derivative shell, for selectively extracting specific materials from the aqueous solution to be treated.

2. A structure according to claim 1 in which the microporous cellulose derivative is water-insoluble and has a porosity of between 60 and 90 percent, and is selected from at least one member of the group consisting of cellulose triacetate, cellulose nitrate, cellulose tripropionate, and ethyl cellulose.

3. A structure according to claim 1 in which the magnetic particles are selected from at least one member of the group consisting of magnetite, barium ferrite, cobalt ferrite, nickel, and magnetic stainless steel.

4. A structure according to claim 1 in which the reactive agent is an ion-selective agent.

5. A structure according to claim 1 in which the reactive agent is an organic-selective agent.

6. A method for forming sorbent magnetic structures comprising the steps of:
(a) forming a solution by dissolving at least one cellulose derivative in a first solvent;
(b) blending a fine powder of magnetic particles into the cellulose-derivative solution to form a slurry;
(c) spraying the slurry in the form of a fine mist; and
(d) collecting a resulting magnetic structure.

7. The method according to claim 6 in which the mist settles into a second solvent liquid coagulant wherein the coagulent is selected from those liquids in which the cellulose derivatives are insoluble but in which the first solvent is soluble.

8. The method according to claim 7 in which the first solvent is selected from at least one member of the group consisting of toluene, diethyl ether, and a low-molecular-weight chlorinated alkane, and the second solvent coagulant is selected from at least one member of the group consisting of water, a lower alcohol, a low-boiling alkane, glycerin, and petroleum ether.

9. The method according to claim 6 in which the cellulose derivative is selected from at least one member of the group consisting of cellulose triacetate, cellulose tripropionate, cellulose nitrate, and ethylcellulose.

10. The method according to claim 6 in which the structures are in the form of microspheres containing from 0.1 to 90% magnetic material, having a diameter of from 5 to 1000 microns, and having a porosity of from 60 to 90%.

11. The method according to claim 6 further comprising dissolving a sorbent solid in a second solvent, wherein said second solvent is soluble in the first solvent, and adding the sorbent solution to the magnetic particle slurry.

12. The method according to claim 11 in which the sorbent solid comprises carnuba wax and the second solvent comprises chloroform.

13. The method according to claim 6 further comprising the step of filling the sorbent magnetic structures with one or more ion-selective agents.

14. The method according to claim 13 in which filling is accomplished by soaking the porous structures in an ion-selective liquid.

15. The method according to claim 13 in which filling is accomplished by soaking the porous structures in a solution of alcohol and titanium tetrachloride, and further comprising the steps of removing the structures magnetically and washing the structures in concentrated ammonium hydroxide.

16. The method according to claim 13 in which filling is accomplished by soaking the porous structures in a nutrient broth containing microorganisms, and further comprising the steps of removing the structures magnetically and allowing the growth of the microorganisms within the pores of the magnetic structures.

17. The method according to claim 13 in which filling is accomplished by soaking the porous structures in a nutrient broth containing microorganisms and further comprising the step of allowing the growth of microorganisms within the pores of the magnetic structures.

* * * * *